(12) United States Patent
Henry et al.

(10) Patent No.: US 12,295,813 B2
(45) Date of Patent: *May 13, 2025

(54) DUAL HEARING PROTECTION SYSTEM

(71) Applicant: 3M INNOVATIVE PROPERTIES COMPANY, St. Paul, MN (US)

(72) Inventors: Paul D. Henry, Carmel, IN (US); David L. Albean, Indianapolis, IN (US); Oscar L. Kårekull, Huskvarna (SE); Cameron J. Fackler, Indianapolis, IN (US); Andreas T. Andersson, Nissafors (SE); Abel Gladstone Mangam, Värnamo (SE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/612,046

(22) Filed: Mar. 21, 2024

(65) Prior Publication Data

US 2024/0225902 A1    Jul. 11, 2024

Related U.S. Application Data

(63) Continuation of application No. 17/765,912, filed as application No. PCT/IB2020/059245 on Oct. 2, 2020, now Pat. No. 11,963,849.

(60) Provisional application No. 62/909,989, filed on Oct. 3, 2019.

(51) Int. Cl.
*H04R 29/00* (2006.01)
*A61F 11/08* (2006.01)
*A61F 11/14* (2006.01)

(52) U.S. Cl.
CPC .............. *A61F 11/14* (2013.01); *A61F 11/08* (2013.01); *A61F 11/145* (2022.01)

(58) Field of Classification Search
CPC .......... A61F 11/14; A61F 11/08; A61F 11/145
USPC ............................................................ 381/56
See application file for complete search history.

(56) References Cited

U.S. PATENT DOCUMENTS

| | | | |
|---|---|---|---|
| 8,649,525 B2 | 2/2014 | Birgersson | |
| 9,020,164 B2 | 4/2015 | Silberman et al. | |
| 9,190,071 B2 | 11/2015 | Butts et al. | |
| 10,165,345 B2 | 12/2018 | Slater et al. | |
| 10,667,954 B2 | 6/2020 | Matossian | |
| 11,741,938 B2 | 8/2023 | Asada et al. | |
| 2008/0240458 A1* | 10/2008 | Goldstein | H04R 1/1083 381/72 |
| 2010/0128885 A1 | 5/2010 | Roos et al. | |

(Continued)

OTHER PUBLICATIONS

International Search Report for PCT Application No. PCT/IB2020/059245 mailed on Dec. 8, 2020, 4 pages.

*Primary Examiner* — William J Deane, Jr.

(57) ABSTRACT

A hearing protection system is provided. The hearing protection system has a first active hearing protection system. The first active hearing protection system is level-dependent. The hearing protection system also has a second active hearing protection system. The second active hearing protection system is level-dependent. Each of the first and second active hearing protection systems are configured to operate in an independent mode and a dual-protection mode. A dual-protection mode level dependent function of the second active hearing protection system is different than an independent mode level dependent function.

20 Claims, 9 Drawing Sheets

(56) References Cited

U.S. PATENT DOCUMENTS

| | | | | |
|---|---|---|---|---|
| 2010/0189277 A1* | 7/2010 | Birgersson | .............. | A61F 11/14 |
| | | | | 381/73.1 |
| 2013/0094685 A1 | 4/2013 | Seo et al. | | |
| 2014/0198932 A1* | 7/2014 | Parkins | ................. | H04R 1/086 |
| | | | | 381/189 |
| 2018/0194055 A1 | 7/2018 | Nerling | | |
| 2019/0130926 A1* | 5/2019 | Giri | ...................... | H04R 1/1083 |
| 2023/0114196 A1* | 4/2023 | Reibner | ................. | A61F 11/12 |
| | | | | 455/518 |
| 2023/0188887 A1* | 6/2023 | Pedersen | ................. | H04R 5/04 |
| | | | | 381/72 |

\* cited by examiner

DUAL HEARING PROTECTION SYSTEM

BACKGROUND

There are two main types of hearing protectors—those intended for wearing over the ear and those intended for wearing within the ear. Some hearing protectors passively reduce sound entering a user's ear, using a sound blocking material. Others have additional electronic circuitry to actively process ambient sound to safe levels.

SUMMARY

A hearing protection system is provided. The hearing protection system has a first active hearing protection system. The first active hearing protection system is level-dependent. The hearing protection system also has a second active hearing protection system. The second active hearing protection system is level-dependent. Each of the first and second active hearing protection systems are configured to operate in an independent mode and a dual-protection mode. A dual-protection mode level dependent function of the second active hearing protection system is different than an independent mode level dependent function.

The above Summary is not intended to describe each illustrated embodiment or every implementation of the present disclosure. Further features and advantages are disclosed in the embodiments that follow. The Drawings and the Detailed Description that follow more particularly exemplify certain embodiments using the principles disclosed herein.

DETAILED DESCRIPTION

Passive hearing protection can be as simple as an expanding foam article intended for placement within a user's ear. Or passive hearing protection can include ear muffs configured for placement over the ear. However, passive hearing protection limits the ability of a user to hear their surroundings. In some scenarios, it may be necessary for a user to hear sound at safe levels nearby, for example voices, footsteps or environmental warning sounds.

Active hearing protection includes one or more microphones that receive ambient sound from a user's surroundings and uses one or more speakers to play it back at a safe level. Active hearing protection devices use electronic circuitry to pick up ambient sound through the microphone and convert them to safe levels before playing it back to the user through a speaker. Additionally, active hearing protection may comprise filtering out undesired sound content, for example actively reducing the sound of a gunshot while providing human speech at substantially unchanged levels.

First, a sound signal is received by a microphone in an active hearing protection unit. The received sound signal is converted to an electronic signal for processing. After processing the sound signal such that all frequencies are at safe levels, the sound signal is reproduced and played back to a user through a speaker.

Some active hearing protection units are level dependent, such that an electronic circuit adapts the sound pressure level. Level dependent hearing protection units help to filter out impulse noises, such as gunshots from surrounding noises, and/or continuously adapt all ambient sound received to an appropriate level before it is reproduced to a user. Active hearing protection units, specifically level dependent active hearing protection units, may be necessary to facilitate communication in noisy environments, or environments where noise levels can vary significantly, or where high impulse sounds may cause hearing damage. A user may need to hear nearby ambient sounds, such as machine sounds or speech, while also being protected from harmful noise levels.

While active hearing protection units can be provided using either ear plugs or ear muff designs, it may not be possible to provide sufficient protection using only one hearing protection device, e.g. ear plugs or ear muffs. However, combining multiple hearing protection devices in an optimal fashion is not as simple as wearing both ear plugs and ear muffs. Active hearing protection includes circuitry that is generally designed to operate independently from any other hearing device. For example, if an active hearing ear muff set is not programmed for a user wearing passive ear plugs, it is possible that the user will not be able to hear the reproduced sound, which will make communication with others difficult.

Additionally, if a user wears both active ear plugs and active ear muffs that are not aware of each other, it is likely that the ear plugs will operate as if receiving ambient sound and further process sound already processed by the earmuffs, resulting in distorted sound. In addition to the sound not being natural, overly distorted sound can cause nausea and discomfort to a user.

If used together, the speaker of a traditional level dependent earmuff will no longer deliver sound directly to the ear canal, as it was designed, which will also distort the acoustic experience. Additionally, the two level dependent functions of the earmuff and earplug will be cascaded, with the acoustic output of the earmuff exciting the acoustic input of the level dependent earplug, resulting in an unpredictable steady-state and transient behavior.

A system is desired that allows for multiple active hearing protection units to be used simultaneously. Each active hearing protection unit should be able to, upon detection of a second active hearing protection unit, enter a dual hearing protection mode such that they coordinate processing of ambient sound to safe levels for a user.

The use of dual hearing protection units in concert allows for greater sound level reduction that either could achieve alone. The sound level reduction is due to the passive sound attenuation of the devices. The gain in the Noise Reduction Rating (NRR) for the double protection combinations ranged from 7-17 dB when compared to the plugs alone, 3-14 dB when compared to the muffs alone, and 3-10 dB when compared to the better of the two individual devices This increase can be achieved by using the two hearing protection units in series such that a second hearing protection unit receives processed sound from a first hearing protection unit. For example, where processing by an active ear muff is sufficient to bring sound to a safe level, an active ear plug may allow the sound to pass through unaltered. However, where ambient noise is too loud, the active ear muff will conduct a first sound processing step and the ear plug will conduct a second sound processing step.

Figure 1:
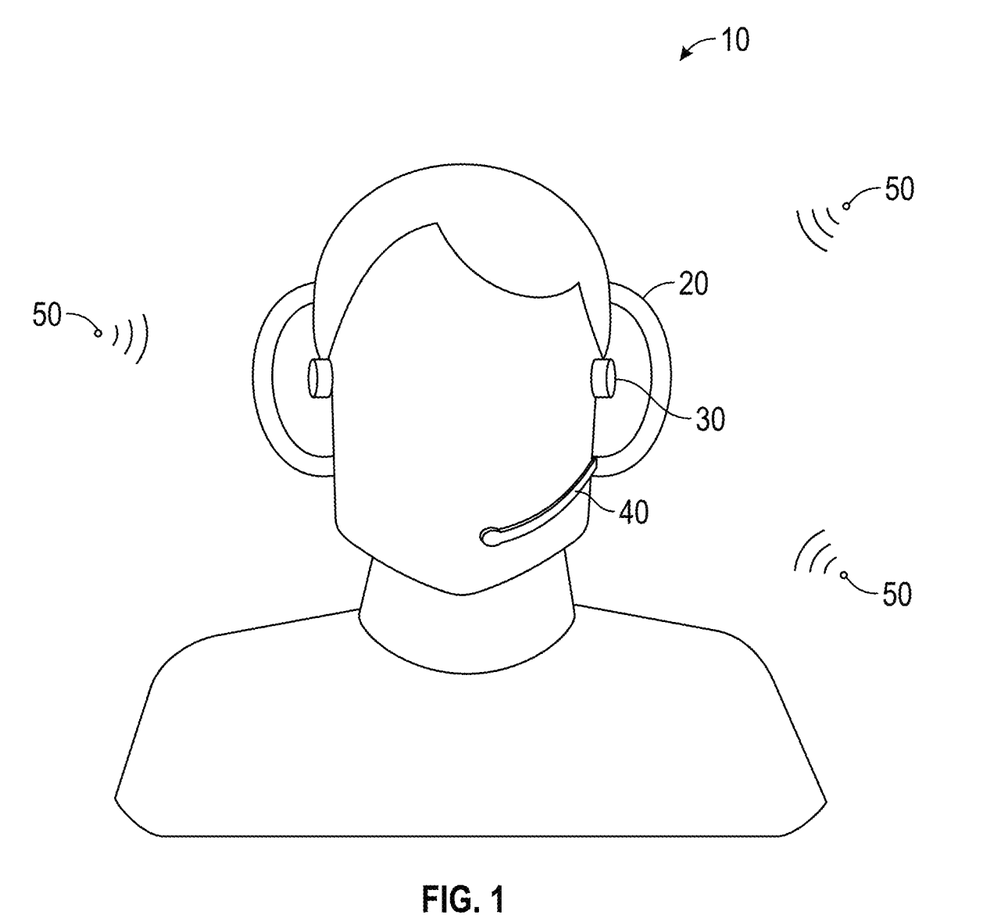
FIG. 1 illustrates a dual hearing protection system in accordance with an embodiment of the present invention.

FIG. 1 illustrates a dual hearing protection system in accordance with an embodiment of the present invention. A person 10 may be in an environment with a plurality of sounds 50. As illustrated in FIG. 1, different sounds 50 may have different noise levels associated with them. Some of noises 50 may be safe to hear at ambient levels, while others are not. In fact, some of sounds 50 may be loud enough that a single hearing protection system is not sufficient to bring them to safe levels.

In one embodiment, person 10 wears both a first hearing protection system 20 and a second hearing protection system 30. First hearing protection system 20 is illustrated as a pair of earmuffs while second hearing protection system 30 is illustrated as a pair of in-ear plugs. First and second hearing protection systems 20, 30 are both active hearing protection systems that are configured to detect each other and, once detected, enter a dual protection mode. While both first and second hearing protection systems 20, 30 are configured to operate as independent level-dependent hearing protection systems, they are also configured to enter a dual protection mode and coordinate hearing protection functionality.

In a dual protection mode, ambient sounds 50 may first be received by first hearing protection system 20. First hearing protection system 20 may conduct a first processing operation and produce a first processed sound. The first processed sound is received by second hearing protection system 30, which conducts a second processing operation to produce a second processed sound, which is provided to user 10. As described herein, 'first processed sound' refers to first hearing protection system 20 providing either an electronic signal directly to the earplug, or providing a sound signal through a speaker which is then picked up by the earplug.

In order for the second processed sound to sound natural to user 10, it is important for first and second hearing protection systems 20, 30 to be aware of each other, and to be programmed to operate in series to achieve additional hearing protection. As described below in greater detail, hearing protection systems 20 and 30 are both configured such that they can detect that another hearing protection system is available and enter a dual protection mode. In the dual protection mode, each of first and second hearing protection systems adjust their operation parameters to compensate for the presence of another hearing protection system. This helps to reduce distortion and other undesired audio artifacts, such as sound pumping, for example. For example, second hearing protection system 30 operates with the awareness that it is receiving a first processed sound signal, not an ambient sound 50, which can reduce distortion that would otherwise be experienced by using two active hearing protection units.

A dual hearing protection system can also include one or more microphones 40. Microphone 40 is illustrated in FIG. 1 as positioned to pick up the voice of user 10. However, other microphones (not shown) may be positioned to pick up ambient sounds 50. Additionally, each of first and second hearing protection systems 20, 30 may have one or more of their own microphones 40.

Figure 2:
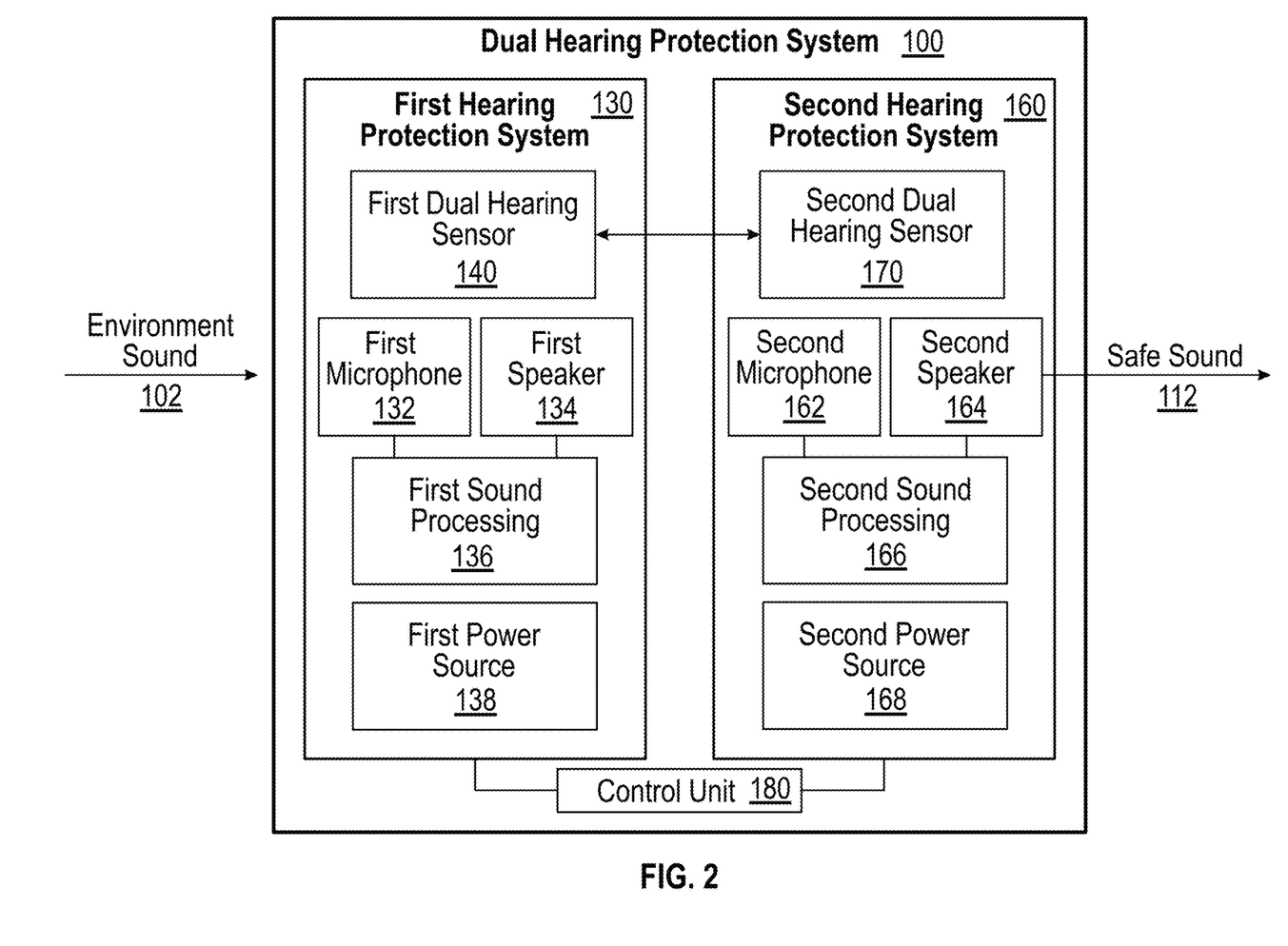
FIG. 2 is a block diagram of a dual hearing protection system in accordance with an embodiment of the present invention.

FIG. 2 is a block diagram of a dual hearing protection system in accordance with an embodiment of the present invention. System 100 may be used in conjunction with other communication devices, such as a microphone (not shown in FIG. 2). System 100 is configured to receive ambient sound 102 from the environment, which may include sustained or impulse sounds at an unsafe level, and communicates sound 112 at a safe level to a user. System 100 includes a first hearing protection system 130 and a second hearing protection system 160, each of which are configured to operate independently. However, in one embodiment, both first and second hearing protection systems 130, 160 are also configured to operate in a dual protection mode.

First hearing protection system 130 includes a first microphone 132 and a first speaker 134. First microphone is configured to receive environmental sounds 102 from around a user. Received environment sounds 102 are converted to an electrical signal, which is then provided by microphone 132 to first sound processor 136. The electronic signal is then compressed by sound processor 136 according to a compression curve such that safe level sounds are still presented at a safe level, and sounds that are too loud are compressed. In some embodiments, some safe level sounds are actually amplified. The processed electronic signal is then converted back to a sound signal, which is provided to a user by a first speaker 134. The compression curves used be each of the first and second hearing systems are different when they operate in the dual protection mode than when they operate in an independent mode.

First hearing system 130, in one embodiment, also has a dual hearing sensor 140, which is configured to detect second hearing system 160. For example, dual hearing sensor 140 may detect a corresponding dual hearing sensor 170 of second hearing system 160, in one embodiment. In another embodiment, sensor 140 is not physically a part of first hearing system 130, but is instead part of another device configured to detect the presence of both first and second hearing systems 130, 160, and provide instructions for first and second hearing systems 130, 160 to enter a dual hearing protection mode. Once second hearing protection system 160 is detected, however, dual hearing sensor 140 may send a command for first hearing protection system 130 to sound processor 136. In an independent mode, sound processor 136 may use a first set of level dependent functions to adjust received sounds 102 to a safe sound level. However, in a dual protection mode, sound processor 136 may use a second set of level dependent functions to adjust received sounds 102 for provision to second hearing protection system 160. For example, a first compression curve, part of the first level dependent function set, may differ from a second compression curve, part of the second level dependent function set. Additional level dependent functionality that may change between the independent and dual hearing protection mode may include equalization, frequency response or other noise reduction functionality.

Second hearing protection system 160 has a second microphone 162 and a second speaker 164. Second microphone 162 is configured to receive processed sound from first speaker 134. Second microphone 162 converts the received processed sound to an electrical signal and provides it to second sound processing unit 166. Second sound processing unit 166 performs a second compression on the sound signal, which is converted to a safe sound signal 112 and provided to a user by second speaker 164. Second hearing protection system 160 is configured to operate in either an independent mode, as a sole hearing protection device, or in a dual hearing protection mode, in conjunction with first hearing protection system 130. Switching second hearing protection system 160 from an independent mode to a dual hearing protection mode is accomplished when dual hearing sensor 170 senses first hearing protection system 130 is also in operation. When operating in a dual hearing protection mode, second sound processing unit 166 uses a different compression curve than when operating in an independent mode. The dual protection mode compression curve used by second sound processor 166 takes into account the compression curve used by first sound processing system 136, such that safe sound 112 is natural and has reduced distortion than if first and second hearing protection systems 130, 160 operated independently.

In one embodiment, both first and second hearing protection systems 130, 160 are level dependent. Both first and second hearing protection systems 130, 160 have a power source, 138 and 168 respectively. However, while power sources 138 and 168 are illustrated as independent power sources, it is also contemplated that a single source could power both first and second hearing protection systems 130, 160.

In one embodiment, a control unit 180 is configured to detect both first and second hearing protection systems 130, 160 and provide the command to enter a dual protection mode for the dual hearing sensors 140, 170. However, while control unit 180 is illustrated as a separate device for clarity, it is contemplated that either first or second hearing protection system 130, 160, could comprise the control unit, such that one system sends the command to the other system. In one embodiment, the command also includes the compression curve to use in the dual hearing protection mode.

While systems 130, 160 are described as single units, it is also expressly contemplated that each comprises two hearing protection units—for example, first hearing protection system 130 can comprise a set of ear muffs configured to be worn over a user's ears, while second hearing protection system 160 can comprise a set of ear plugs, configured to be worn within a user's ears. In the embodiment where second hearing protection system 160 comprises two unconnected ear plugs, it is contemplated that control unit 180 could be located in any of the ear muffs, the left ear plug, or the right ear plug.

Figure 3:
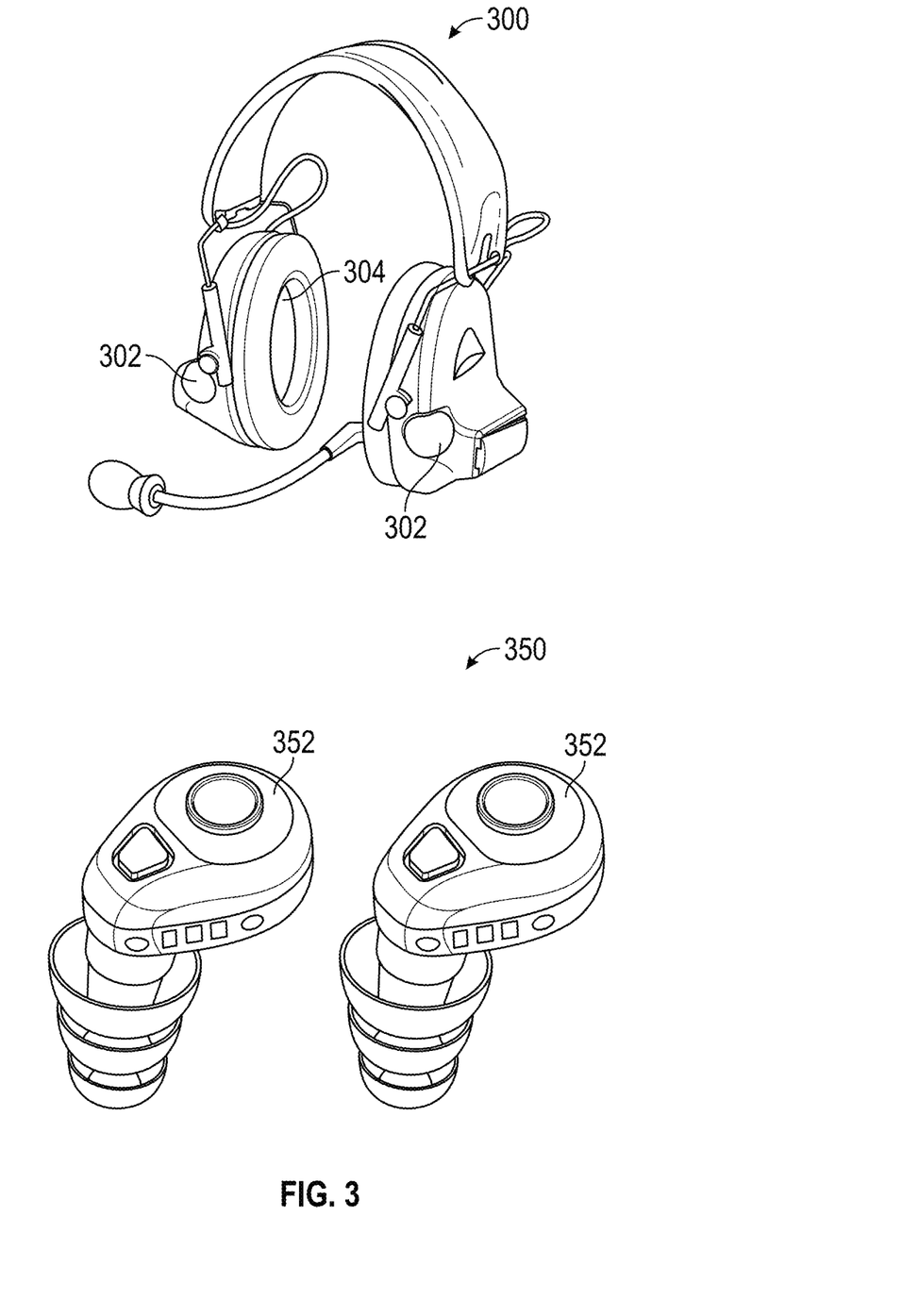
FIG. 3 illustrates a diagram of elements of a dual hearing protection system in accordance with an embodiment of the present invention

FIG. 3 illustrates a diagram of elements of a dual hearing protection system in accordance with an embodiment of the present invention. As illustrated in FIG. 3, ear muff system 300 and ear plug set 350 are configured to operate independently as well as in a dual protection mode. Ear muff system 300 has microphones 302, which are configured to pick up ambient sounds for processing to safe levels. Each ear plug in ear plug set 350 also has a microphone 352. When operating independently, microphones 352 are configured to pick up ambient environmental noise for processing to safe levels. However, in a dual protection mode, microphones 352 are configured to receive processed sound from ear muff system 300, for example from a corresponding speaker 304 within an ear muff.

Figure 4:
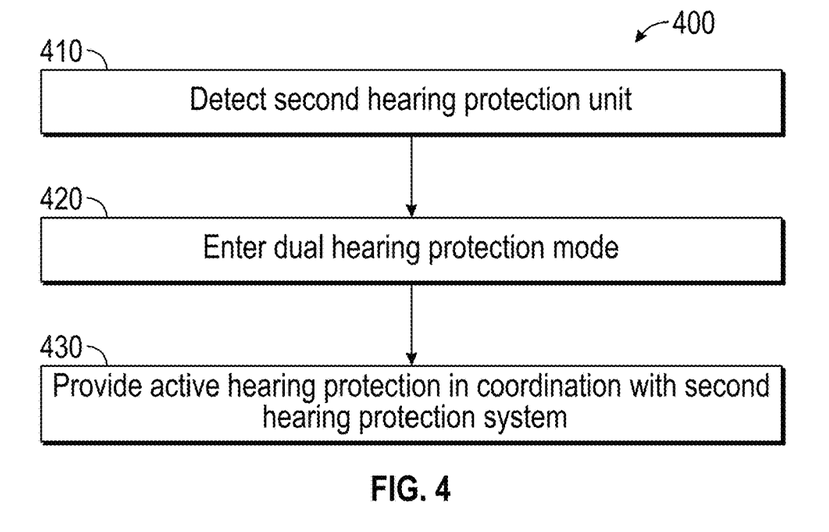
FIG. 4 illustrates a method of entering a dual hearing protection mode for a system of hearing protection units.

FIG. 4 illustrates a method of entering a dual hearing protection mode for a system of hearing protection units. Method 400 may be useful, for example, for two level-dependent hearing protection systems that are configured to operate either in an independent mode or in a dual protection mode.

In block 410, a first hearing protection system detects a second hearing protection system. First and second hearing protection systems may be selected from either an active ear plug hearing protection system or an active ear muff hearing protection system. Detection may comprise a first hearing protection system directly detecting the presence of the second hearing protection system, in one embodiment. In another embodiment, detection may comprise a first hearing protection system detecting a network and, through the network, becoming aware of a second hearing protection system.

In block 420, both first and second hearing protection systems enter a dual hearing protection mode. For example, each system may be configured, after powering up, to operate in an independent mode and only enter a dual protection mode when a second hearing protection system is detected. Alternatively, each system may be configured, after powering up, to search for and enter a dual protection mode if a second hearing protection system is found.

In block 430, active hearing protection is provided to a user. In one embodiment, both first and second hearing protection systems are configured to perform a level dependent operation on sound, at least at some sound levels. For example, if sound below 80 decibels (dB) is considered safe, first hearing protection system may compress a 100 dB sound to 85 dB, while second hearing protection system takes the 85 dB sound and compresses it to 76 dB. However, if an ambient sound is detected at 85 dB, first hearing protection system may compress it to 76 dB, and second hearing protection system may pass the signal through to a user without any significant additional compression. In another embodiment, however, both first and second hearing protection systems are configured to perform a compression operation, such that, for example, the 85 dB sound is first compressed to 80 dB and then compressed to 76 dB.

Figure 5:
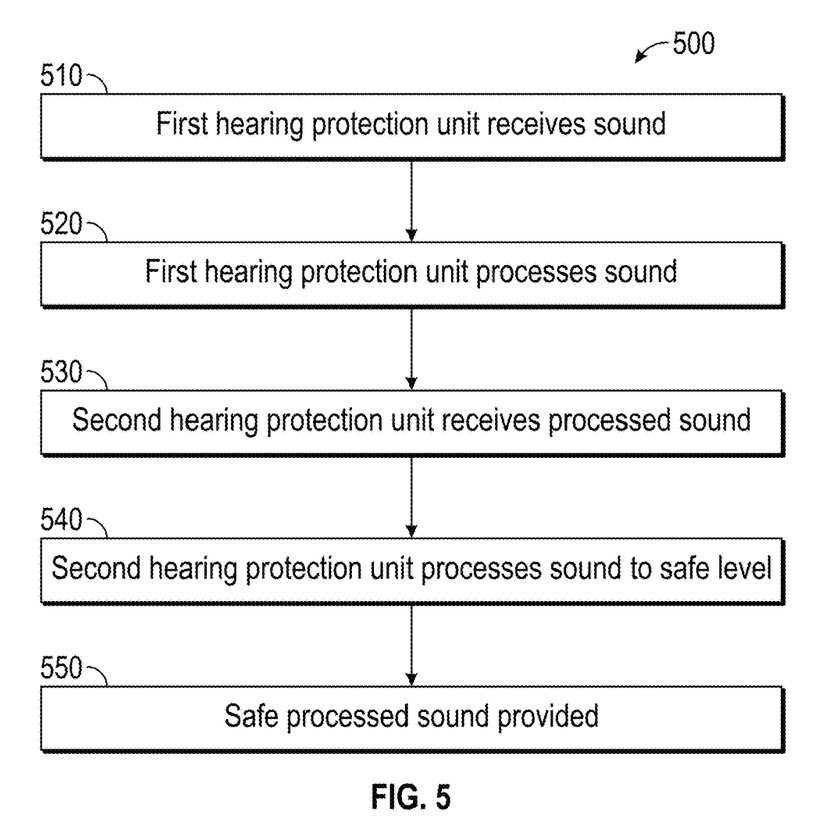
FIG. 5 illustrates a method of processing sound to a safe level using a dual hearing protection system.

FIG. 5 illustrates a method of processing sound to a safe level using a dual hearing protection system. Method 500 may be useful for two level dependent hearing protection devices operating as a single dual hearing protection system. In one embodiment, each of the two, level dependent hearing protection devices are configured to operate either independently, if used alone, or in a dual protection mode, when used in accordance with method 500.

In block 510, a first hearing protection unit receives ambient sound. For example, the first hearing protection unit is a level dependent earmuff unit configured to be worn around a user's ear, while a second hearing protection unit is a level dependent ear plug configured to be worn within a user's ear, such that a microphone of the level dependent ear plug is wholly within the level dependent earmuff unit. In one embodiment, the level dependent earmuff unit will coordinate functionality between the right and left earplugs.

In block 520, the first hearing protection unit processes the received sound. For example, processing may comprise converting the sound signal to an electronic signal and then compressing the electronic signal. Processing may also comprise equalizing sounds within the electronic signal. Additional processing may also be conducted. After the processing step is complete, the electronic signal is converted back to a sound signal by a speaker of the first hearing protection unit.

In block 530, a processed sound signal is received by the second protection unit. The sound signal may be transferred by a speaker of the first hearing protection unit to a microphone of the second hearing protection unit.

In block 540, the processed sound signal undergoes a second processing step. Because the first and second protection units are operating in a dual hearing protection mode, the second processing step is completed in the context of the completed first processing step. For example, the second hearing protection unit is aware of the compression curve used by the first processing unit. The second hearing protection unit is also aware of the acoustic scenario in which the sound signal is transferred—e.g. that the second hearing protection unit is not receiving ambient noises, but a sound recording that has already undergone some processing and may have some distortion.

In block 550, sound processed to a safe level is provided to a user through a speaker of the second hearing protection unit. The first and second hearing protection unit are configured to operate in concert to provide a sound that is as natural and undistorted as possible. Method 500 accomplishes this by using two hearing protection units that are operating in a dual hearing protection mode. Because the two hearing protection units are aware of how the other will behave, they can process the ambient sounds to a safe level without the distortion that would be created using two level dependent hearing protection units operating independently.

Method 500 is described with respect to two processing steps, 520 and 540. However, it is expressly contemplated that, in some embodiments, either of first or second hearing protection unit allows sound to be transferred without significant alteration. For example, if a user is in a relatively quiet environment, no compression may be needed and both the first and second hearing protection units may receive and transmit ambient sound without alteration. In an area with loud, but near safe sound levels, only one compression step may be necessary, such that either first or second hearing protection system receives and transmits sound without significant alteration. For some very loud sounds, however, both first and second hearing protection units may provide compression. The benefit of using two hearing protection systems is that, in concert, greater hearing protection can be provided.

Figure 6:
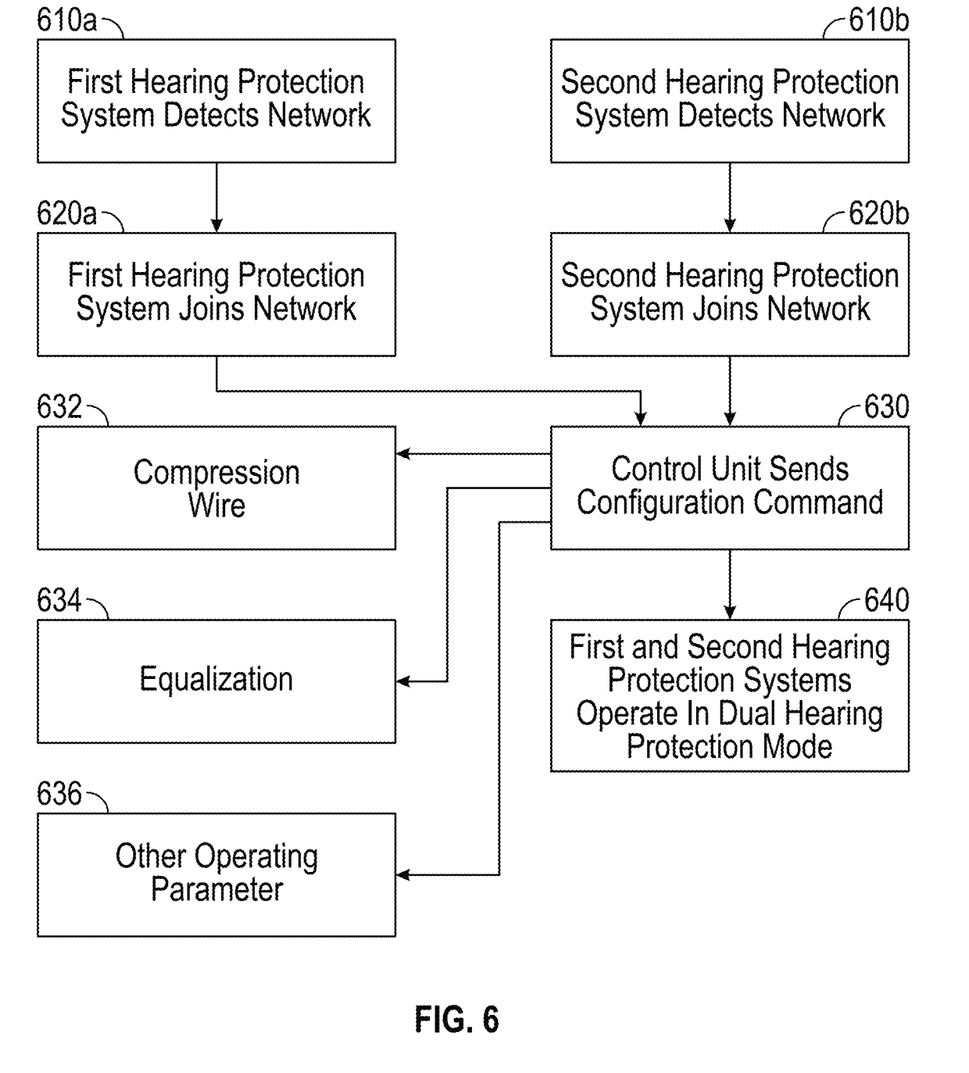
FIG. 6 illustrates a method of processing sound to a safe level using a networked dual hearing protection system.

FIG. 6 illustrates a method of processing sound to a safe level using a networked dual hearing protection system. Method 600 illustrates how multiple hearing protection devices may operate within a network. While systems and methods have been described thus far in the context of a communications system that only contains first and second hearing protection devices, it is contemplated that such devices may operate in concert with other devices. For example, in addition to providing sound to a wearer of the two hearing protection devices, a copy of the sound signal may also be transmitted elsewhere and/or recorded on a separate device.

In blocks 610*a* and 610*b*, each of a first and second hearing protection system becomes aware of a network. This may happen, for example, when each is turned on (which may be simultaneously or sequentially), in one embodiment. In another embodiment, a hearing protection unit only searches for a network when directed by a user, for example by turning on a network search feature. In one embodiment, either first or second hearing protection system creates and maintains the network in step 610*a* or 610*b*, such that only the other hearing protection unit needs to become aware of a nearby network. In one embodiment, one of the first and second hearing protection systems is a master system which determines which devices are allowed to join the network. In the event that both the first and second hearing protection systems have joined a network, in one embodiment, the master system causes both to enter a dual-hearing protection mode.

In block 620*a* and 620*b*, each of the first and second hearing protection systems joins a network. The network may be a near field network, a wireless network, a wired network, or any other suitable network. One of the first or second hearing protection systems may not need to undergo this step, for example in the embodiment where one of the systems creates the network.

In another embodiment, a control unit is aware of a first and second hearing protection systems on a network. In one embodiment, the control unit is one of the first or second hearing devices, and becomes aware of a second hearing protection system. In another embodiment, the control unit is responsible for maintaining the network, and in each of blocks 620*a* and 620*b*, joins each of a first and second hearing protection system to the network.

In block 630 the control unit sends a command such that the first and second hearing protection systems enter a dual hearing protection mode. In the dual hearing protection mode, each of the first and second hearing protection systems operates in concert with the other. The command to enter a dual hearing mode may include instructions regarding new compression curves 632, new equalization parameters 634, and/or other parameters 636, such as, for example, how volume adjustments are made. In one embodiment, the new parameters 632, 634, 636 are stored by the first and second hearing protection devices, and the command only instructs the devices to access stored parameters and switch modes. However, in another embodiment the control unit stores the parameters and sends them as part of the command to enter a dual hearing protection mode.

In one embodiment, the control unit is one of the hearing protection devices. For example, the control unit may be one of the two ear plugs, and may be connected to the other ear plug and/or to the ear muff system using a master-slave relationship. However, masterless control schemes are also envisioned.

The network of method 600 may comprise a personal area network. The personal area network may utilize near field magnetic induction. However, other network configurations are also possible, such as, but not limited to, WIFI, local area network, near field communication, Bluetooth(R) and Bluetooth low energy, zigbee, thread, z-wave and others.

In block 640, the first and second hearing protection systems operate in the dual hearing protection mode. Operating in the dual hearing protection mode includes each of first and second hearing protection systems operating in concert to process ambient sounds to safe levels. In one embodiment, this includes the first and second hearing protection modes operating in series, such that the first hearing protection system receives ambient sound, processes it a first time and then provides it to the second hearing protection system for a second processing step before it is provided to a user.

Embodiments described herein provide systems and methods for using two hearing protection devices to reproduce sound at safe levels for a user. Embodiments described herein require the first and second hearing protection devices to work in concert to produce a more natural sound than would be produced from two hearing protection devices working independently from each other.

Because different hearing protection devices are not normally designed to work with each other, embodiments described herein rely on a dual protection mode of operation for both the first and second hearing protection devices. If each device were to operate independently, problems would arise as the ear plugs would not be aware that the sounds they received were already processed. The resulting distortion could create unnatural sound, discomfort and nausea. Additionally, the two independent systems would create instability and have nondeterministic responses.

At some levels, where only one compression operation is required to reduce ambient sounds to safe levels, the ear plug system is configured to operate as if it is acoustically transparent in a dual protection mode. However, at sound levels where two compression levels are required, the ear plug system will stop being acoustically transparent and will conduct a second processing step.

The two hearing protection devices are both level-dependent, in one embodiment such that they can coordinate volume control and result in a combined volume adjustment between the two devices that would be unavailable from the two devices independently. The use of dual hearing protection units in concert allows for greater sound level reduction that either could achieve alone. The sound level reduction is due to the passive sound attenuation of the devices. For example, level dependent earmuffs, used by themselves, can achieve anywhere between 20-30 noise reduction rating. Level dependent earplugs, used by themselves, can achieve anywhere between 8-30 noise reduction rating. The gain in the noise reduction rating for the double protection combinations ranged from 7-7 dB when compared to the plugs alone, 3-14 dB when compared to the muffs alone, and 3-10 dB when compared to the better of the two individual devices In one embodiment, in the dual hearing protection mode, the level dependent function of the ear plugs is disabled, such that the ear plug hearing device is acoustically transparent at some sound levels. However, at higher sound levels, the level dependent ear plug exhibits non-linear behavior. To avoid cascaded level dependent functions, however, when the level dependent earplug exhibits non-linear behavior, the level dependent functionality of the ear muff will be reduced. In some embodiments, the level dependent functionality of the ear muff is reduced such that it is essentially turned off.

In one embodiment, such functionality is achieved by a hard limiter, such that, above a certain sound pressure level, sounds are clipped to a particular threshold. Additionally, the amplifier is disabled when the sound pressure level inside the cup reaches a certain threshold, the level dependent earplug amplifier turns off until the sound inside the ear muff falls below the certain threshold. Additionally, the ear plug contains a modified level dependent function that, when combined with the earmuff level dependent functionality, works to create a smooth downward decay of sound for a user. In one embodiment, this is implemented in the level dependent ear plug by monitoring the sound pressure level inside the earmuff to control the sound output. In another embodiment, the level dependent functions of the earmuffs and earplugs communicate over a channel to pass compression parameters that produce an overall desirable compression curve. The channel is, in one embodiment, wired. In another embodiment, the channel is wireless.

EMBODIMENTS

Embodiment 1 is a hearing protection system that includes a first active hearing protection system and a second active hearing protection system. The first active hearing protection system is level-dependent. The second active hearing protection system is level-dependent. One of the first and second active hearing protection systems can operate in either an independent mode or a dual-protection mode. A dual-protection mode level dependent function of the second active hearing protection system is different than an independent mode level dependent function.

Embodiment 2 includes the features of embodiment 1, however the first active hearing protection system is a set of earmuffs.

Embodiment 3 includes the features of any of embodiments 1 or 2, however the second active hearing protection system is a set of earplugs.

Embodiment 4 includes the features of any of embodiments 1-3, however the second active earing protection system receives processed sound from the first active hearing protection system.

Embodiment 5 includes the features of any of embodiments 1-4, however the second active hearing protection system is substantially acoustically transparent at some sound levels.

Embodiment 6 includes the features of any of embodiments 1-5, however the first active hearing protection system receives ambient environment sounds and conduct a first processing operation, and the second active hearing protection system receives a processed sound from the first processing operation and conduct a second processing operation.

Embodiment 7 includes the features of any of embodiments 1-6, however each of the first and second active hearing protection systems comprise a microphone and a speaker.

Embodiment 8 includes the features of any of embodiments 1-7, however it also includes a control unit configured to detect the first and second active hearing protection systems.

Embodiment 9 includes the features of embodiment 8, however the control unit is part of the first active hearing protection system.

Embodiment 10 includes the features of embodiment 8, however the control unit is part of the second hearing protection system.

Embodiment 11 includes the features of any of embodiments 8-10, however the control unit is configured to send a command to switch from the independent mode level dependent function to the dual-protection mode level dependent function.

Embodiment 12 includes the features of embodiment 11, however the control unit is also configured to send the dual-protection mode level dependent function parameters to the first active hearing protection system or the second active hearing protection system.

Embodiment 13 includes the features of any of embodiments 11-12, however the control unit is also configured to send the dual-protection mode level dependent parameters to both the first active hearing protection system and the second active hearing protection system.

Embodiment 14 includes the features of any of embodiments 1-13, however it also includes a network to which both the first and second active hearing protection systems are connected.

Embodiment 15 includes the features of any of embodiments 1-14, however the independent and dual mode level dependent function parameters comprise an independent and dual mode compression curve, respectively.

Embodiment 16 includes the features of any of embodiments 1-15, however the independent and dual mode level dependent function parameters comprise an independent and dual mode equalization parameter, respectively.

Embodiment 17 is a method of processing sound to a safe level using a dual protection hearing system. The method includes detecting, using a first hearing protection unit, an ambient sound. The method also includes processing, using the first hearing protection unit, the ambient sound. The method also includes receiving, by a second processing unit, the processed ambient sound. The processed ambient sound is received from the first hearing protection unit. The method also includes processing, using the second hearing protection unit, the processed sound. The method also includes providing the dual processed sound from the second hearing protection unit to a user of the dual protection hearing system.

Embodiment 18 includes the features of embodiment 17, however the first hearing protection unit is a set of earmuffs.

Embodiment 19 includes the features of any of embodiments 17-18, however the first hearing protection unit is a set of earplugs.

Embodiment 20 includes the features of any of embodiments 17-19, however the first and second hearing protection units are configured to operate in either an independent mode or a dual protection mode. A level dependent processing parameter for both the first and second hearing protection units are different in the dual protection mode than in the independent mode.

Embodiment 21 includes the features of embodiment 20, however the level dependent processing parameter comprises a compression curve.

Embodiment 22 includes the features of any of embodiments 20-21, however the level dependent processing parameter comprises an equalization parameter.

Embodiment 23 includes the features of any of embodiments 17-22, however both the first and second processing units are level dependent.

Embodiment 24 includes the features of any of embodiments 17-23, however, at some sound levels, the second hearing protection unit is substantially acoustically transparent such that the processed sound and the dual processed sound are substantially identical.

Embodiment 25 includes the features of any of embodiments 17-24, however the received processed sound is an electronic signal provided by a processor.

Embodiment 26 includes the features of any of embodiments 17-25, however the received processed sound is a sound signal provided by a speaker.

Embodiment 27 is a method of operating a dual hearing protection system. The method includes detecting a first hearing protection system and a second hearing protection system. The method also includes joining the first and second hearing protection systems to a network. The method also includes sending a command to the first and second hearing protection systems to switch from an independent mode to a dual protection mode. A dual protection mode sound processing parameter of the first or second hearing protection system is different than an independent mode sound processing parameter.

Embodiment 28 includes the features of embodiment 27, however the second hearing protection system, in the independent mode, is configured to receive ambient sound for processing and, in the dual protection mode, is configured to receive processed sound from the first hearing protection system for processing.

Embodiment 29 includes the features of any of embodiments 27-28, however the first hearing protection system is an earmuff unit.

Embodiment 30 includes the features of any of embodiments 27-29, however the second hearing protection system is an earplug set.

Embodiment 31 includes the features of any of embodiments 27-30, however the first and second hearing protection systems are level dependent.

Embodiment 32 includes the features of any of embodiments 27-31, however the network is generated by the first hearing protection system.

Embodiment 33 includes the features of embodiment 32, however the network is generated by the left earplug.

Embodiment 34 includes the features of embodiment 32, however the network is generated by the right earplug.

Embodiment 35 includes the features of any of embodiments 27-34, however the network is generated by a control unit separate from the first and second hearing protection units.

Embodiment 36 includes the features of any of embodiments 27-35, however the sound processing parameter is a compression curve.

Embodiment 37 includes the features of any of embodiments 27-36, however the sound processing parameter is an equalization parameter.

Embodiment 38 includes the features of any of embodiments 27-37, however at some sound levels the second hearing protection system is substantially acoustically transparent.

Embodiment 39 is a method of switching operational modes for a dual hearing protection system. The method includes operating a first hearing protection unit in an independent mode, using an independent mode level dependent parameter. The method also includes detecting a second hearing protection unit. The method also includes switching the first hearing protection unit from the independent mode to a dual hearing protection mode. The dual hearing protection mode comprises the first hearing protection mode using a first level dependent parameter and the second hearing protection mode using a second level dependent parameter.

Embodiment 40 includes the features of embodiment 39, however, in the dual protection mode, the first hearing protection unit is configured to receive ambient sound, process the ambient sound, and provide processed sound to the second hearing protection unit.

Embodiment 41 includes the features of embodiment 40, however, in the dual protection mode, the second hearing protection unit is configured to receive the processed sound from the first hearing protection unit and provide a safe sound to a user of the dual hearing protection system.

Embodiment 42 includes the features of embodiment 41, however, in the dual protection mode, the second hearing protection unit is acoustically transparent at some sound levels.

Embodiment 43 includes the features of embodiment 41, however, in the dual protection mode, the second hearing protection unit is configured to, for at least some ambient sounds, process the received sound. The processed received sound is the safe sound.

Embodiment 44 includes the features of any of embodiments 39-43, however the first hearing protection unit is a set of earmuffs.

Embodiment 45 includes the features of any of embodiments 39-44, however the second hearing protection unit is a set of earplugs.

Embodiment 46 includes the features of any of embodiments 39-45, however detecting comprises a control unit.

Embodiment 47 includes the features of embodiment 46, however the control unit is part of the first hearing protection unit.

Embodiment 48 includes the features of embodiment 46, however the control unit is part of the second hearing protection unit. Detecting a second hearing protection unit comprises the control unit joining a network.

Embodiment 49 includes the features of embodiment 48, however the second hearing protection unit is a set of earplugs, and wherein the control unit is part of the left earplug.

Embodiment 50 includes the features of embodiment 48, however the second hearing protection unit is a set of earplugs, and wherein the control unit is part of the right earplug.

Embodiment 51 includes the features of any of embodiments 39-50, however detecting comprises the first hearing protection unit being part of a network and detecting that the second hearing protection unit has joined the network.

Embodiment 52 includes the features of embodiment 51, however the network is created by a control unit.

Embodiment 53 includes the features of any of embodiments 39-52, however the level dependent parameter comprises a compression curve.

Embodiment 54 includes the features of any of embodiments 39-53, however the level dependent parameter comprises an equalization parameter.

Embodiment 55 is a dual hearing system that includes a system network. The system also includes a first hearing protection unit configured to operate in an independent mode and a dual protection mode and a second hearing protection unit configured to operate in an independent mode and a dual protection mode. Upon detecting that both the first and second hearing protection units have joined the system network, each of the first and second hearing protection units switch from operating in the independent mode to operating in the dual protection mode.

Embodiment 56 includes the features of embodiment 55, however operating in an independent mode comprises using an independent mode level dependent parameter, and operating in a dual protection mode comprises using a dual protection mode level dependent parameter.

Embodiment 57 includes the features of embodiment 56, however a second hearing protection unit dual protection mode compression curve is configured such that, at some sound levels, the second hearing protection unit is acoustically transparent.

Embodiment 58 includes the features of any of embodiments 55-57, however in the dual protection mode, the second hearing protection unit is configured to receive processed sound from the first hearing protection unit.

Embodiment 59 includes the features of any of embodiments 55-58, however the first hearing protection unit comprises an earmuff unit and the second hearing protection unit comprises a set of earplugs.

Embodiment 60 includes the features of embodiment 59, however the earmuff unit comprises a controller configured to manage the system network.

Embodiment 61 includes the features of embodiment 59, however the set of earplugs comprises a controller configured to manage the system network.

Embodiment 62 includes the features of embodiment 61, however the left earplug comprises a controller configured to manage the system network.

Embodiment 63 includes the features of embodiment 61, however the right earplug comprises a controller configured to manage the system network.

Embodiment 64 includes the features of any of embodiments 55-63, however it also includes a control unit configured to send a command to each of the first and second hearing protection units to switch from the independent mode to the dual protection mode.

Embodiment 65 includes the features of embodiment 64, however the command to the first hearing protection unit also comprises the first dual mode level dependent parameter. The command to the second hearing protection unit also comprises the second dual mode level dependent parameter.

Embodiment 66 includes the features of any of embodiments 55-65, however the independent mode level dependent parameter comprises an independent mode compression curve.

Embodiment 67 includes the features of any of embodiments 55-66, however the independent mode level dependent parameter comprises an independent mode equalization parameter.

EXAMPLES

Example 1

Figure 7A:
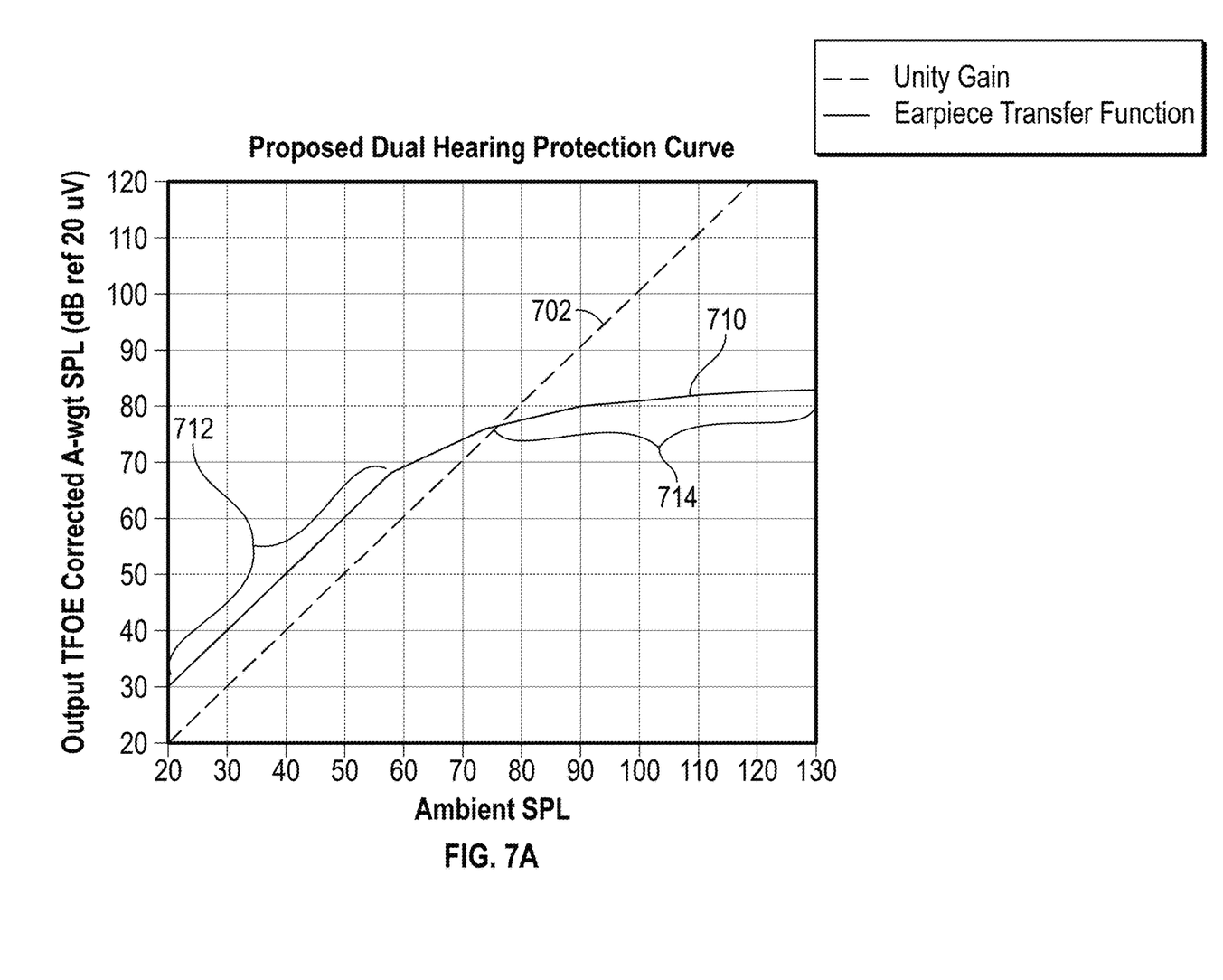
FIGS. 7A-7D illustrate example sound attenuation curves discussed in the Examples.

FIG. 7A illustrates sound pressure level (in SPL) coming into a hearing protection system in the x-axis, and sound pressure level (SPL) coming out of the hearing protection system on the y-axis. Line 702 represents a unity gain, or no transformation of the sound pressure level as it is processed by the hearing protection system. Data above line 702 represents amplification while data below line 702 represents attenuation. A slope greater than the dotted line represents expansion, while a slope below the line represents compression.

Curve 710 represents a level dependent function of a typical earmuff-style protection device on a high gain setting. For low sounds, as indicated by range 712, there is a 10 dB amplification, such that 40 dB in results in 50 dB out. For higher sounds, as indicated by range 714, the sound undergoes compression, such that 100 dB in results in 80 dB out, for example. However, the compression range 714 does not necessarily have a linear compression rate.

Figure 7B:
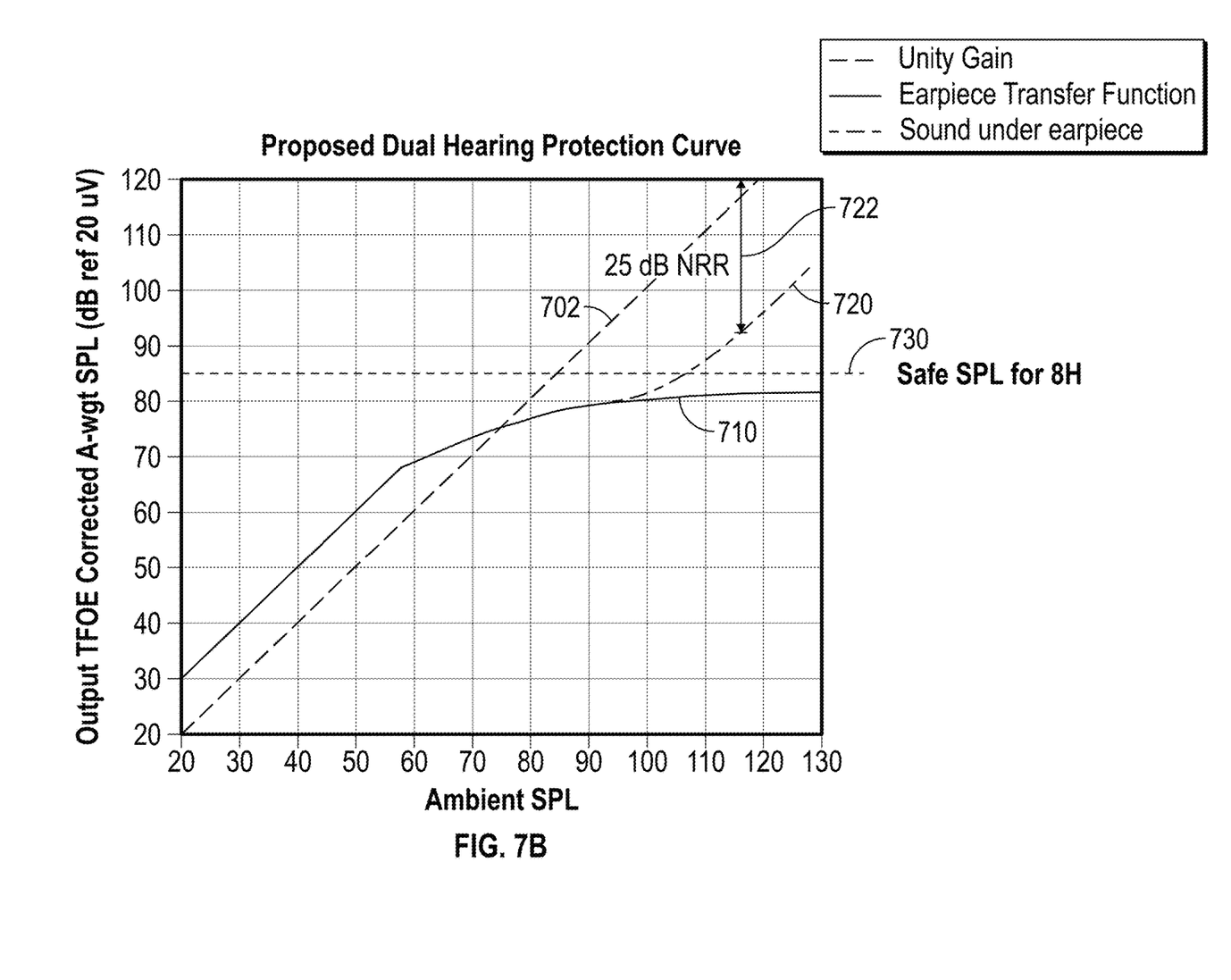

FIG. 7B illustrates the earmuff transfer function 710 as well as the actual sound 720 present under an earmuff. As indicated by line 730, 85 dB is considered a safe sound limit for 8 hour exposure. The earmuff hearing protection device used has an NRR of 25 dB, as indicated by difference 722. This results in actual sound under the earmuff 720, representing sound produced by electronics and ambient sound passing through the earmuff, that rises above the safe level for incoming sounds higher than 108 dB.

Example 2

Figure 7C:
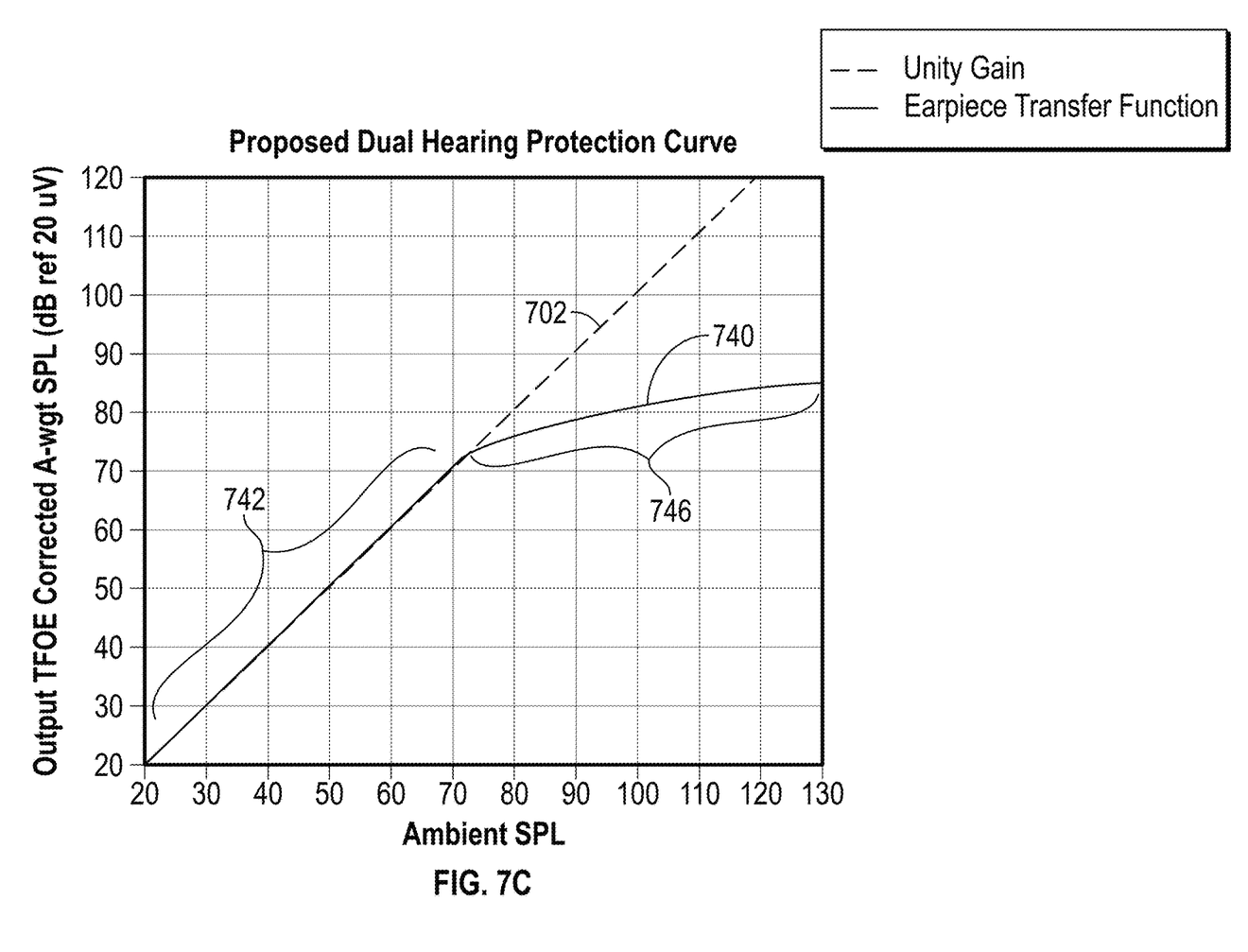

FIG. 7C illustrates an earpiece transfer function 740. As compared to FIG. 7A, the earpiece transfer function for earpiece differs from that of the earmuff in a dual hearing protection mode. The earpiece approximates a unity gain for low to moderate sounds, as indicated by range 742, which reduces the combined gain effects from wearing two devices. The earpiece is acoustically 'invisible' below 76 dB, which allows the overall response to be completely controlled by the earmuff. However, in range 744, the transfer function aggressively asymptotes to 85 dB. This allows an earplug to provide additional attenuation in loud sound fields when the earmuff alone is inadequate.

Figure 7D:
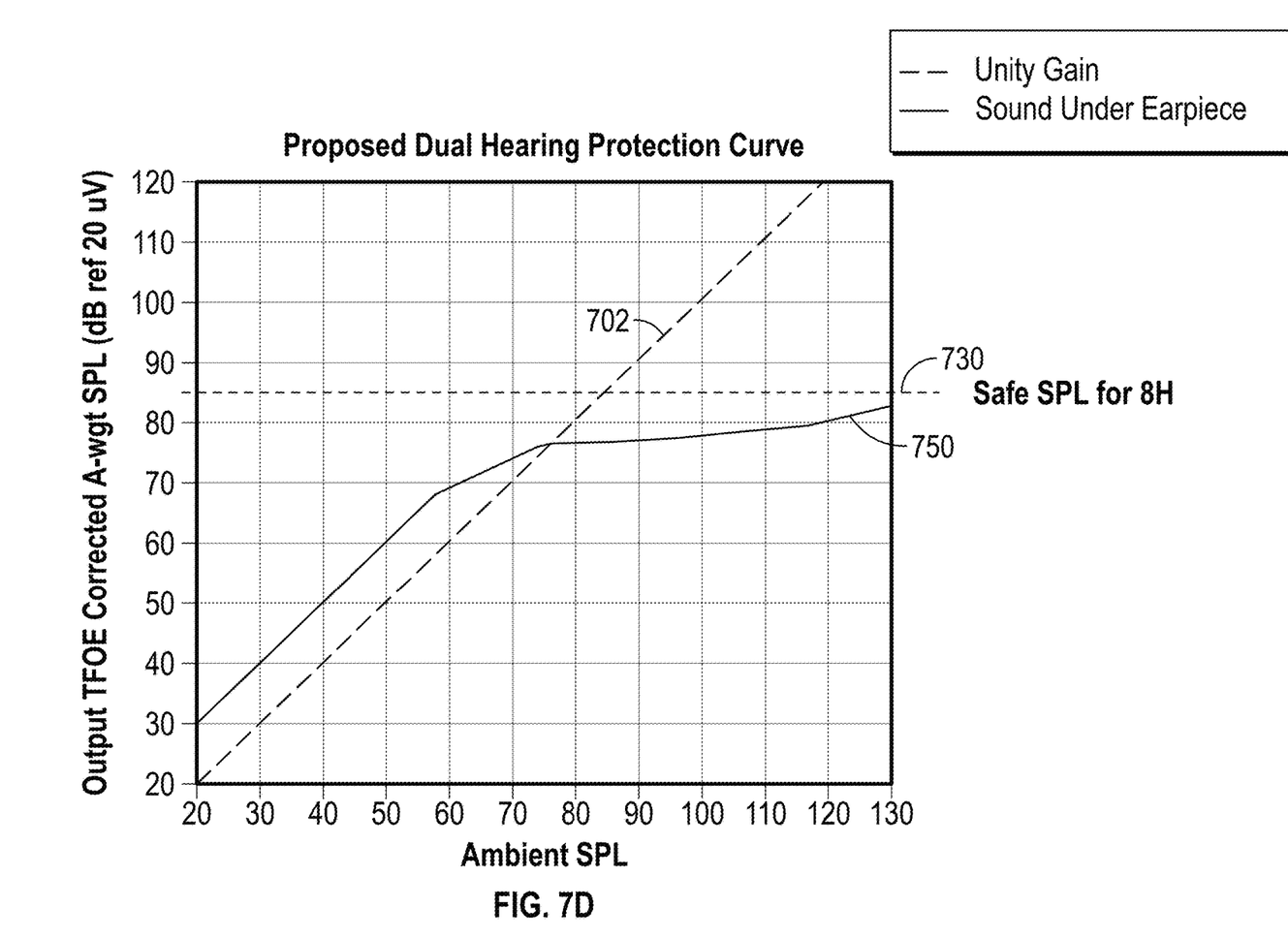

FIG. 7D illustrates the actual sound 750 under the earpiece, as experienced by a user of the dual hearing protection system. The actual sound curve 750 follows the earmuff curve for low level sounds, has a "soft compression knee" to minimize audible artifacts, and provides further compression of the sound under the earcup, shown in FIG. 7B, to below 85 dB.

What is claimed is:

1. A method of operating a dual hearing protection system, the method comprising: detecting a first hearing protection system and a second hearing protection system; joining the first and second hearing protection systems to a network;

sending a command to the first and second hearing protection systems to switch from an independent mode to a dual protection mode;

causing the first hearing protection system to enter the dual protection mode;

causing the second hearing protection system to enter the dual protection mode;

wherein a dual protection mode sound processing parameter for the first hearing protection system is different than an independent mode sound processing parameter for the first hearing protection system; and  wherein, in the dual protection mode, the first and second hearing protection systems coordinate a first sound processing operation of the first hearing protection system with a second sound processing operation of the second hearing protection system.

2. The method of claim 1, wherein the second hearing protection system, in the independent mode, is configured to receive ambient sound for processing and, in the dual protection mode, is configured to receive processed sound from the first hearing protection system for processing.

3. The method of claim 1, wherein the first hearing protection system is an earmuff unit or a pair of earplugs.

4. The method of claim 1, wherein the first and second hearing protection systems are level dependent.

5. The method of claim 1, wherein the network is generated by the first hearing protection system.

6. The method of claim 1, wherein the network is generated by a control unit separate from the first and second hearing protection units.

7. A method of switching operational modes for a dual hearing protection system, the method comprising:

operating a first hearing protection unit in an independent mode, using an independent mode level dependent parameter;

detecting a second hearing protection unit within a network, the network comprising the first hearing protection unit;

switching the first hearing protection unit from the independent mode to a dual hearing protection mode;

wherein the dual hearing protection mode comprises the first hearing protection mode using a dual mode level dependent parameter, different from the independent mode level parameter; and  wherein, in the dual hearing protection mode, the first active hearing protection system conducts a first sound processing operation, the second active hearing protection system conducts a second sound processing operation, and wherein the first and second processing operations are coordinated.

8. The method of claim 7 wherein, in the dual protection mode, the first hearing protection unit is configured to:

receive ambient sound;

process the ambient sound; and provide processed sound to the second hearing protection unit.

9. The method of claim 8, wherein, in the dual protection mode, the second hearing protection unit is configured to:

receive the processed sound from the first hearing protection unit; and provide a safe sound to a user of the dual hearing protection system.

10. The method of claim 7, wherein the first hearing protection unit is a set of earmuffs or a set of earplugs.

11. The method of claim 1, wherein detecting comprises a control unit detecting the second hearing protection system joining the network.

12. The method of claim 11, wherein the control unit is part of the first hearing protection unit.

13. The method of claim 11, wherein the network is created by the control unit.

14. A hearing protection system comprising:

a first hearing protection system configured to join a network, the first hearing protection system comprising a first level dependent sound processing unit;

a second hearing protection system configured to join the network, the second hearing protection system comprising a second level dependent sound processing unit;

a network controller configured to generate the network, wherein the network controller is configured to, when the first and second hearing protection systems have joined the network, generate a command for the first and second hearing protection systems to switch from an independent operating mode to a dual hearing protection mode;

wherein, in the dual hearing protection mode, the first and second level dependent sound processing units coordinate processing of an ambient sound to a safe level for a user.

15. The hearing protection system of claim 14, wherein the command comprises a command for each of the first and second hearing protection systems to access a stored parameter for the dual hearing protection mode, wherein the stored parameter is different from an independent hearing protection mode parameter.

16. The hearing protection system of claim 14, wherein the command comprises a dual mode compression curve or a dual mode equalization parameter.

17. The hearing protection system of claim 14, wherein the network is a personal area network.

18. The hearing protection system of claim 14, wherein the network controller is configured to send the command when the second hearing protection unit is detected in the network.

19. The hearing protection system of claim 14, wherein the network controller is separate from both the first and second hearing protection systems.

20. The hearing protection system of 14, wherein the network controller is configured to initiate the network.

* * * * *

UNITED STATES PATENT AND TRADEMARK OFFICE
CERTIFICATE OF CORRECTION

PATENT NO. : 12,295,813 B2
APPLICATION NO. : 18/612046
DATED : May 13, 2025
INVENTOR(S) : Paul Dishaun Henry Page 1 of 1

It is certified that error appears in the above-identified patent and that said Letters Patent is hereby corrected as shown below:

In the Claims

<u>Column 16</u>
Line 54, In Claim 20, delete "The hearing protection system of 14" and insert -- The hearing protection system of claim 14 --, therefor.

Signed and Sealed this
Sixteenth Day of December, 2025

John A. Squires
*Director of the United States Patent and Trademark Office*